(12) United States Patent
Rubin et al.

(10) Patent No.: US 7,153,989 B2
(45) Date of Patent: Dec. 26, 2006

(54) PROCESS FOR PREPARING CONJUGATED LINOLEIC ACID

(76) Inventors: David Rubin, 8949 Montrose Way, San Diego, CA (US) 92122; Eyal Rubin, 8949 Montrose Way, San Diego, CA (US) 92122

( * ) Notice: Subject to any disclaimer, the term of this patent is extended or adjusted under 35 U.S.C. 154(b) by 0 days.

(21) Appl. No.: 11/053,891

(22) Filed: Feb. 10, 2005

(65) Prior Publication Data

US 2006/0178521 A1 Aug. 10, 2006

(51) Int. Cl.
*C11B 3/00* (2006.01)
(52) U.S. Cl. .................................... 554/183
(58) Field of Classification Search ............... 554/186
See application file for complete search history.

(56) References Cited

U.S. PATENT DOCUMENTS

| 2,838,480 | A | 6/1958 | Swern et al. |
| 4,481,145 | A | 11/1984 | Timms |
| 4,792,418 | A | 12/1988 | Rubin et al. |
| 6,303,547 | B1 | 10/2001 | Balasubramaniam |
| 6,602,908 | B1 | 8/2003 | Seidel |

*Primary Examiner*—Deborah D. Carr
(74) *Attorney, Agent, or Firm*—Browdy and Neimark, PLLC

(57) ABSTRACT

Trans-9,cis-11-octadecadienoic acid is produced by forming a urea inclusion complex with cis-linoleic acid, treating the complex with a catalytic amount of a base, and recovering the trans-9,cis-11 octadecadienoic acid. Tans-10,cis-12-octadecadienoic acid is produced by iodinating cis-linoleic acid at temperatures of about −5–20° C. A mixture of trans-9,cis-11 octadecadienoic acid and trans-10,cis-12-octadecadienoic acid comprising is produced by iodinating cis-linoleic acid at temperatures ranging from about 50 to about 90° C.

6 Claims, No Drawings

PROCESS FOR PREPARING CONJUGATED LINOLEIC ACID

FIELD OF THE INVENTION

The present invention relates to a process for preparing conjugated linoleic acid.

BACKGROUND OF THE INVENTION

Conjugated linoleic acid is a general term used to name positional and geometric isomers of linoleic acid. Conjugated linoleic acid (CLA) differs from ordinary linoleic acid in that ordinary linoleic acid has double bonds at carbon atoms 9 and 12. The common denominator of these conjugated acids is that there in only one single bond between the two double bonds. Examples of CLA include cis- and trans-isomers (E/Z isomers) of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid, 10,12-octadecadienoic acid, and 11-13-octadecadienoic acid. The conjugated forms are considered more stable than the non-conjugated forms from a thermodynamic point of view.

While there are many possible cis-trans possible isomers, two forms are most abundant: trans,9-cis,11-octadecadienoic acid and trans,10-cis,12-octadecadienoic acid. In ruminant animals, certain bacteria in the rumen covert the linoleic acid of vegetable oils mainly to the trans,9-cis,11-octadecadienoic acid, which is why it is called rumenic acid.

In the areas of health and nutrition, researchers have shown that ingestion of conjugated fatty acids may inhibit tumor growth, prevent heart disease, and reduce body fat. There is a great deal of interest in the apparent health benefits imparted by certain conjugated linoleic acids. CLAs, originally isolated from the fat and milk of ruminants, exhibit impressive physiological effects in animal studies. In a variety of chemical forms, including but not limited to free fatty acids and fatty acid methyl esters, CLA reportedly has antidiabetic properties, leads to reduced carcinogenesis and atherosclerosis, and increases bone and muscle mass.

Conjugated linoleic acid has a significant potency relative to other fatty acids with respect to modulating tumorigenesis. As noted above, conjugated linoleic acid is closely related to linoleic acid but differs from linoleic acid in the position and configuration of the double bonds. Linoleic acid has a stimulatory effect on carcinogenesis, as contrasted with the ability of conjugated linoleic acid to inhibit tumor development. In this way, conjugated linoleic acid has the opposite effect of linoleic acid in treating carcinomas. In fact, conjugated linoleic acid has a significant potency relative to other fatty acids in modulating tumorigenesis.

The terms "conjugated linoleic acid" and "CLA" as used herein are intended to include 9,11-octadecadienoic acid, 10,12-octadecadienoic acid, and mixtures thereof. The non-toxic salts of the free acids may be made by reacting the free acids with a non-toxic base.

Conjugated linoleic acid has long been of interest to biochemists and nutritionists. An article in *Inform*, Vol. 7(2): 1996, published by the American Oil Chemists' Society, summarizes some of the data developed to that date. The article stresses the feed use for which the product was being developed, resulting in less fat and more lean meat in animals. A number of other recent articles stress the effects of CLA in fighting cancer. In many cases, one isomer, 9,11-CLA has been named as the active isomer, mainly because it alone is incorporated into the phospholipids of the organisms being fed CLA.

CLA has also been shown to have preventive effects on breast cancer in mice. CLA is not currently used for humans as a medication because it is only available in an impure form. Impurities in CLA can have a detrimental influence on toxicity tests required to obtain FDA approval.

Since CLA occurs naturally in foodstuff the FDA did not remove it from the market, but the FDA never approved the claims for its benefits.

According to Turner, *Food Product Design*, October, 2003, a 50/50 blend of CLA isomers impacts a person's body mass by reducing body fat while maintaining lean muscle mass when ingested at a recommended daily intake level of 3 grams.

The c9-11 isomer is associated with anticarcinogenic properties, possibly providing benefits in all three stages of caner, namely initiation, promotion, and metastasis.

The January, 2003 issue of *Journal of Nutrition* reports results of a human study conducted by Martha Belury, professor of human nutrition at Ohio State University, Columbus, that revealed the t-10,c-12 isomer impacted adult-onset (type 2) diabetes by lowering the subjects' body mass as well as blood sugar levels.

Gaullier et al., *American Journal of clinical Nutrition* 79:1, 118–125, 2004, reviewed various human health studies that investigated the effect of CLA on body composition. The research involved doses of CLA (50:50 mixtures of c-9,t-11 and t-10,C-12 isomers) ranging from 3 to 7 grams of CLA per day and treatment period running from four weeks to one year. Fat losses of up to 9% were reported, as well as 2–3% increases in lean mass.

Further benefits of CLA include the following:
 Increases metabolic rate
 Decreases abdominal fat
 Enhances muscle growth
 Lowers cholesterol and triglycerides
 Reduces food-induced allergic reactions
 Enhances the immune system A factor hampering commercialization and research interest in CLA is that these compounds are not naturally abundant. Conjugated polyenes are typically present in animal fats only at a level of about 0.5 percent. Conjugated polyenes do not occur widely in plants.

Several methods exist for preparing conjugated fatty acids, including biosynthesis, dehydration of hydroxy fatty acids, and isomerization. Biosynthetic methods have been used to prepare a number of conjugated dienes. This technique was the results of a discovery that bacteria found in the stomachs of ruminants convert dietary unsaturated fatty acids contained in plant food sources into conjugated isomers. For example, the enzyme linoleate isomerase, isolated from the rumen anaerobic bacterium *Butyrivibrio fibrisolvens*, isomerized linoleic acid to main cis-9, trans-11-octadecadienoic acid, or rumenic acid. However, biosynthetic methods are not preferred for several reasons, including generally low yields and the difficulty of isolating specific conjugated compounds from the mixture that results.

In preparing conjugated fatty acids via dehydration of hydroxy fatty acids, various isomers can be obtained. However, although these methods produce yields that are somewhat better than biosynthetic methods, yields seen in such dehydrogenation methods nevertheless are still less than about 70%.

Synthesis of conjugated fatty acids via isomerization typically proceeds from an unconjugated polyene fatty acid or fatty acid ester as precursor, particularly linoleic acid. According to the delta nomenclature system, linoleic acid can be expressed as all-cis-9,12-octadecadienoic acid or c-9,c-12-octadecadienoic acid.

Isomerization produces various isomers that have the same atomic composition as the parent compound but that differ in chemical structure. Isomerization of linoleic acid could produce a total of at least eight isomers: two positional isomers, α9,11 and α10,12. Each of the positional isomers could appear as four geometric isomers: c-9,c-11; c-9,t-11; t-9, t-11- and t-9,c-11; and c-10,c-12-, c-10,t-12-, t-10,c-12, and t-10,t-12.

Isomerization of unconjugated polyenes to produce conjugated polyenes can be accomplished in several ways, including photochemically, by means of metallic ion or metal carbonyl catalysts, treatment with acids, and treatment with strong bases.

A typical photosensitization process involves irradiating an unconjugated precursor with light of a suitable wavelength range in a solvent and optionally in the presence of a suitable photosensitizer. Disadvantages of this method include the need for special equipment and the need to remove residual photosensitizer from the final product. Moreover, yields obtained typically are only about 80%.

Double-bond migrations can also take place by means of treatment with metallic ions (most often, complexes containing Pd, Pt, Rh or Ru) or metal carbonyl catalysts. This type of isomerization proceeds according to one of two possible mechanisms. The first mechanism, known as the metal-hydride addition-elimination reaction, requires external hydrogen. The second method, called the α-allyl complex mechanisms, does not require external hydrogen. In either case, however, the transition metals typically required in this type of isomerization are expensive and sometimes toxic.

Double-bond rearrangements can also take place upon treatment with acids. This type of isomerization follows a two-step mechanism, in which one of the double-bonded carbon atoms first gains a proton, giving a carbocation, and then the methylene unit adjacent to the other doubly-bonded carbon atom loses a proton, causing a double bond to re-form. The most thermodynamically stable isomer is the one predominantly formed during isomerization. Acid-catalyzed isomerization is not a preferred method, however, because carbocations generate many side products in addition to the desired conjugated isomers.

The most common isomerization methods used to produce conjugated fatty acids involve treatment of unsaturated fatty acids with strong base. As in the case of the acid-catalyzed isomerization reaction, base-catalyzed isomerization produces equilibrium mixtures of the most thermodynamically stable isomers. Base-catalyzed double bond isomerization, sometimes called prototropic rearrangement, is an example of electrophilic substitution with accompanying allylic rearrangement. Because the double bond of the unconjugated substrate can shift to be in conjugation with the one already present, the double bond will migrate that way because the conjugated configuration is more thermodynamically stable.

Various methods can be used to produced conjugated fatty acids by base-catalyzed isomerization of an unconjugated fatty acid, but all of these methods have certain drawback. For example, A.O.C.S. Official Method Cd 7-58, produced conjugated compounds by adding a solution of potassium hydroxide in ethylene glycol to an unconjugated substrate in a weight ratio of about 110:1 and maintaining the reaction at 180° C. for 25 minutes. This process uses a considerable excess of alkali metal hydroxide catalyst, adding expense and presenting safety concerns.

Another problem with many CLA products made by conventional approaches is their heterogeneity, and substantial variation from batch to batch. Commercial preparations contain between 50 and 75% of CLA. Commercial CLA is generally made from safflower oil, which oil contains a substantial amount of linoleic acid. However, the reaction used for conversion of cis-linoleic acid to CLA takes place at very high temperatures (200–250° C.). This high temperature converts the oleic acid to 50% trans-oleic acid, a compound known to be atherogenic and carcinogenic. Other processes for preparing CLA produce essentially a combination of about 48% trans-9,cis-11 and 47% trans-10,cis-12 conjugated linoleic acids, and the balance consists of other isomers of unknown biological activity. Therefore, there exists a great need for biologically active CLA products of defined composition.

SUMMARY OF THE INVENTION

It is an object of the present invention to overcome the aforesaid deficiencies in the prior art.

It is another object of the present invention to provide a process for preparation of conjugated linoleic acid.

It is yet another object of the present invention to provide a process for preparation of conjugated linoleic acid isomers substantially free of impurities.

It is another object of the present invention to provide methods for ameliorating the effects of carcinoma in a human.

It is a further object of the present invention to provide methods for improving insulin sensitivity.

According to the present invention, linoleic acid is added to a saturated solution of urea in ethanol at temperatures of from about 60 to about 80° C. to form an inclusion molecule. Addition of catalytic amounts of a base such as KOH, NaOH sodium methoxide or potassium methoxide converts the partially included cis linoleic acid-urea molecule preferentially to trans-9,cis-11-octadecadienoic acid.

Iodination-diiodination of cis linoleic acid in aqueous tetrahydrofuran at about −5 to about 10° C. preferentially converts the cis linoleic acid to the trans-10,cis-12 isomer. When the same reaction is conducted at about 50–90° C., and preferring about 50–70° C., there is no preference, and the two isomers are produced in substantially equal amounts. At even higher temperatures, the concentration of the two isomers is reduced, and at least six other isomers are produced.

The process of the present invention has the following advantages:

A simple method to produce a specific isomer

A simple method to produce a substantially pure combination of the desired isomers.

The reactions take place at relatively low temperatures, thus preventing formation of peroxides and polymers.

Starting with the free fatty acid rather than the triglyceride results in higher concentration of the end products and eliminates the impurities and undesirable effects of isomerization of other fatty acids.

DETAILED DESCRIPTION OF THE INVENTION

Separation of cis Linoleic Acid from Vegetable Oil

Vegetable oils are a rich source of cis linoleic acid, with safflower oil being the richest (about 70 to 80%).

1. Saponification

To a mixture of 200 g safflower oil, 400 mL ethanol was added. A solution of 50 g KOH in 400 mL of water was added, and the mixture was stirred at about 60° C. for 90 minutes, until a clear solution appeared. Alternatives to KOH include but are not limited to NaOH KOMe, NaOMe similar bases. One liter of water was then added, then 250 cc of dichloromethane. The solution was shaken vigorously and then separated in a separation funnel. All non-saponified materials (i.e., sterols) were dissolved in the dichloromethane, while the soap of the fatty acids remained in the aqueous phase. Then 180 mL of 1 M sulfuric acid was added to the separated aqueous phase. The free fatty acids were separated form the aqueous phase to create an organic phase.

2. Elimination of cis Linoleic Acid

The fatty acids were dissolved in 95% ethanol and an aqueous solution of 5M NaOH was added. The temperature was reduced to about 0° C. The sodium salts of the saturated fatty acids (stearic and palmitic) and the oleic acid precipitated and were removed by filtration. A solution of 1M of HCl was added to obtain the cis linoleic acid. This results in product of 98.5–99% linoleic acid, yielding 80% of the theoretical value.

3. Formation of the trans-9,cis-11-isomer

Two hundred mL of free cis linoleic acid was added dropwise to a saturated solution of urea in 95% ethanol at about 60° C. The mixture was shaken for one hour, and 10 grams of sodium methoxide (NaOH, KOH or Potassium methoxide can be used instead of sodium methoxide) in 100 cc of ethanol were added. The solution was left to react for four hours and then cooled to about 0° C. for twelve hours. The white crystals of the inclusion urea-fatty acids were separated by filtration, and shaken in warm water to dissolve the urea. The organic phase was washed and dried on anhydrous MgSO$_4$. After preparation of the methyl ester, gas chromatography indicated about 98% trans-9,cis-11-isomer.

4. Formation of the trans-10,cis-12-isomer (iodination-diiodination Process)

One hundred grams of cis linoleic acid was dissolved in 1500 mL of tetrahydrofuran (THF) Alternative solvent for this step include but are but are limited to acetonitride and dimethylformamide. A solution of 26 g of sodium sulfite and 80 g of potassium bicarbonate sodium bicarbonate in 800 cc of water was added with vigorous stirring. After 10 minutes, 40 g of iodine was added and the mixture was stirred at about 5° C. for 48 hours. The reaction was quenched with a solution of 66 g potassium bicarbonate and 50 g potassium sulfate in one liter of water. Alternative quenching salts include but are not limited to sodium bicarbonate and sodium sulfate. The mixture was then extracted twice with 800 cc of ethyl acetate and concentrated in 1500 cc hexane. The extract was washed twice with water and separated in a separatory funnel and evaporated to remove the hexane.

5. Diiodination

One hundred grams of the iodinated product was reacted with 24 grams of chlorotrimethylsilane and 100 g of sodium iodide in one liter of acetonitrile as solvent. The reaction was maintained at about 23° C. for 30 minutes. The reaction was quenched by the addition of a solution of 100 g sodium sulfite and 50 g sodium citrate in 500 mL water. Other quenching salts include but are not limited to potassium sulfate and potassium citrate. (The Potassium Salts)

The solution was vigorously shaken with hexane. After drying to remove hexane and drying on a 4 Ang. molecular sieve, desired product was obtained as 85% yield of 93% trans-10,cis-12-isomer.

When the iodination reaction was conducted as above but at 60° C., the yield was a mixture of the two main isomers, 79% yield of 96% combined CLA. These isomers can be separated from each other or can be marketed as a combination of isomers.

The purified CLA of the present invention is useful in treating carcinoma by therapeutically administering to potassium sulfite a patient in need thereof a therapeutically effective amount of the purified t-10, C-12 isomer.

The present invention also provides a method for treating and suppressing diabetes in a human or other animal by administering to a patient in need thereof a therapeutically effective amount of the purified c-9,c-11 isomer prepared by the process of the present invention in which a complex is formed between urea and cis linoleic acid in ethanol, addition of catalytic amounts of a base to convert the cis-linoleic acid preferentially to the t-9,c-11 isomer or by iodinating-diiodinating cis-linoleic acid to form the trans-10,cis-12 isomer.

It is to be understood that the phraseology or terminology employed herein is for the purpose of description and not of limitation. The means and materials for carrying out disclosed functions may take a variety of alternative forms without departing from the invention. Thus, the expressions "means to . . . " and "means for . . . " as may be found the specification above, and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above, and it is intended that such expressions be given their broadest interpretation.

What is claimed is:

1. A method for preparing trans-9,cis-11-octadecadienoic acid comprising:
   a. reacting cis-linoleic acid with a saturated solution of urea in ethanol at 60–80° C. to form an inclusion molecule;
   b. adding catalytic amounts of a base to convert the partially included cis linoleic acid-urea molecule preferentially to trans-9, cis-11 octadecadienoic acid; and
   c. recovering the trans-9,cis-11-octadecadienoic acid.

2. The method according to claim 1 wherein the base is selected from the group consisting of NaOH, KOH, sodium methoxide and potassium methoxide.

3. A method for preparing trans-10,cis-12-octadecadienoic acid comprising:
   a. reacting cis-linoleic acid with iodine;
   b. adding a salt to quench the reaction; and
   c. recovering trans-10,cis-12-octadecadienoic acid.

4. A method for preparing a mixture of trans-9,cis-11-octadecadienoic acid and trans-10, cis-12-octadecadienoic acid comprising:
   a. reacting cis-linoleic acid with iodine at about 50–70 C.
   b. adding a salt to quench the reaction; and
   c. recovering a mixture of trans-9,cis-11-octadecadienoic acid and trans-10,cis-12-octadecadienoic acid.

5. The method according to claim 4 wherein the salt is selected from the group consisting of potassium bicarbonate, sodium bicarbonate, potassium sulfate, sodium sulfate, sodium sulfite, sodium citrate, potassium sulfite, and potassium citrate.

6. The method according to claim 3 wherein the salt is selected from the group consisting of potassium bicarbonate, sodium bicarbonate, potassium sulfate, sodium sulfate, sodium sulfite, sodium citrate, potassium sulfite, and potassium citrate.

* * * * *